United States Patent
Alzamzmi et al.

(10) Patent No.: US 11,992,331 B2
(45) Date of Patent: May 28, 2024

(54) NEONATAL PAIN IDENTIFICATION FROM NEONATAL FACIAL EXPRESSIONS

(71) Applicant: University of South Florida, Tampa, FL (US)

(72) Inventors: Ghadh Alzamzmi, North Bethesda, MD (US); Dmitry Goldgof, Lutz, FL (US); Rangachar Kasturi, Tampa, FL (US); Terri Ashmeade, Tampa, FL (US); Yu Sun, Tampa, FL (US); Rahul Paul, Tampa, FL (US); Md Sirajus Salekin, Tampa, FL (US)

(73) Assignee: University of South Florida, Tampa, FL (US)

( * ) Notice: Subject to any disclaimer, the term of this patent is extended or adjusted under 35 U.S.C. 154(b) by 800 days.

(21) Appl. No.: 17/073,568

(22) Filed: Oct. 19, 2020

(65) Prior Publication Data

US 2021/0030354 A1 Feb. 4, 2021

Related U.S. Application Data

(63) Continuation of application No. PCT/US2019/028277, filed on Apr. 19, 2019.

(60) Provisional application No. 62/660,038, filed on Apr. 19, 2018, provisional application No. 62/660,072, filed on Apr. 19, 2018.

(51) Int. Cl.
*A61B 5/00* (2006.01)
*A61B 5/1171* (2016.01)
*G06N 3/02* (2006.01)

(52) U.S. Cl.
CPC .......... *A61B 5/4824* (2013.01); *A61B 5/1176* (2013.01); *G06N 3/02* (2013.01); *A61B 2503/045* (2013.01)

(58) Field of Classification Search
None
See application file for complete search history.

(56) References Cited

U.S. PATENT DOCUMENTS 5,810,392 A 9/1998 Gagnon
5,844,488 A 12/1998 Musick
(Continued)

FOREIGN PATENT DOCUMENTS

CA 2986863 A1 * 5/2018 ......... G06K 9/00228
CN 107358180 A 11/2017
(Continued)

OTHER PUBLICATIONS

Machine Translation of CN 107392109 A, Clarivate Analytics, 10 pages, printed on Aug. 21, 2023. (Year: 2003).*
(Continued)

*Primary Examiner* — Matthew Kremer
(74) *Attorney, Agent, or Firm* — Molly L. Sauter; Smith & Hopen, P.A.

(57) ABSTRACT

A Neonatal CNN (N-CNN) is provided for detecting neonatal pain emotion based upon facial recognition. A cascaded N-CNN is trained using a Neonatal Pain Assessment Database (NPAD) to automatically identify a neonatal patient experience pain in real-time. These results show that the automatic recognition of neonatal pain provided by the embodiments of the present invention is a viable and more efficient alternative to the current standard of pain assessment.

17 Claims, 3 Drawing Sheets

(56) References Cited

U.S. PATENT DOCUMENTS

| | | | |
|---|---|---|---|
| 6,067,019 | A | 5/2000 | Scott |
| 7,142,697 | B2 | 11/2006 | Huang et al. |
| 8,764,650 | B2 | 7/2014 | Schiavenato et al. |
| 10,827,973 | B1 | 11/2020 | Alzamzmi et al. |
| 2006/0128263 | A1 | 6/2006 | Baird |
| 2008/0235030 | A1 | 9/2008 | Sisto et al. |
| 2012/0088985 | A1 | 4/2012 | Schiavenato et al. |
| 2014/0276188 | A1 | 9/2014 | Jardin |
| 2015/0269424 | A1* | 9/2015 | Bacivarov ............ G06V 40/175 382/203 |
| 2016/0117587 | A1* | 4/2016 | Yan .......................... G06N 3/08 706/20 |
| 2017/0098122 | A1 | 4/2017 | el Kaliouby et al. |
| 2017/0109571 | A1* | 4/2017 | McDuff ................. G06V 10/50 |
| 2017/0140253 | A1* | 5/2017 | Wshah ................... G06V 20/54 |
| 2017/0140260 | A1* | 5/2017 | Manning ............... G06N 3/045 |
| 2018/0039745 | A1* | 2/2018 | Chevalier .............. G16H 30/20 |
| 2018/0289334 | A1* | 10/2018 | De Brouwer .......... G06N 5/046 |

FOREIGN PATENT DOCUMENTS

| | | | |
|---|---|---|---|
| CN | 107491740 A | 12/2017 | |
| IN | 107392109 A | 11/2017 | |
| JP | 2016186802 A | 10/2016 | |
| WO | WO-2008153194 A1 * | 12/2008 | ............... G06N 3/08 |
| WO | 2014036263 A1 | 3/2014 | |
| WO | WO-2017151206 A1 * | 9/2017 | ............... B25J 9/161 |

OTHER PUBLICATIONS

Hudson-Barr et al., Validation of the Pain Assessment in Neonates (PAIN) Scale with the Neonatal Infant Pain Scale (NIPS), Neonatal Network, vol. 21, No. 6, pp. 15-21, Oct. 2002 (Year: 2002).*

Backus, Annette L., "Validation of the Neonatal Infant Pain Scale" (1996). Masters Theses. 280. https://scholarworks.gvsu.edu/theses/280 (Year: 1996).*

Lakshminarayan et al., Three-level Training of Multi-Head Architecture for Pain Detection, 2020 15th IEEE International Conference on Automatic Face and Gesture Recognition (FG 2020), Nov. 2020.

Li et al., Infant Monitoring System for Real-Time and Remote Discomfort Detection, IEEE Transactions on Consumer Electronics, vol. 66, No. 4, Nov. 2020.

Li et al., Video-based Discomfort Detection for Infants Using a Constrained Local Model, IWSSIP 2016—The 23rd International Conference on Systems, Signals and Image Processing. May 23-25, 2016, Bratislava, Slovakia.

Lu et al., Learning Pyramidal Hierarchical Features for Neonatal Face Detection, 2018 14th International Conference on Natural Computation, Fuzzy Systems and Knowledge Discovery (ICNC-FSKD), 2018.

Mansor et al., Pain Assessment Using Neural Network Classifier, 2012 International Symposium on Instrumentation & Measurement, Sensor Network and Automation (IMSNA), 2012, pp. 377-379.

Monwar et al., Pain Recognition Using Artificial Neural Network, 2006 IEEE International Symposium on Signal Processing and Information Technology, 2006, pp. 28-33.

Parodi et al., Automated Newborn Pain Assessment Framework Using Computer Vision Techniques, in Proceedings of the International Conference on Bioinformatics Research and Applications 2017, pp. 31-36. 2017.

Sun et al., Automatic and Continuous Discomfort Detection for Premature Infants in a NICU Using Video-Based Motion Analysis, 2019 41st Annual International Conference of the IEEE Engineering in Medicine and Biology Society (EMBC), pp. 5995-5999. IEEE, 2019.

Sun et al., Respiration Monitoring for Premature Neonates in NICU, Applied Sciences 9, No. 23, 2019, 5246.

Sun et al., Automated discomfort detection for premature infants in NICU using time-frequency feature-images and CNNs, Proc. SPIE 11314, Medical Imaging 2020: Computer-Aided Diagnosis, 113144B, Mar. 16, 2020.

Villarroel et al., Non-contact physiological monitoring of preterm infants in the Neonatal Intensive Care Unit, Nature Partner Journals, Digital Medicine (2019) 128.

Werner et al., Automatic Recognition Methods Supporting Pain Assessment: a Survey, Submission to IEEE Trans. on Affective Computing, vol. X, No. Y, Jul. 2019.

Xu et al., Towards Automated Pain Detection in Children using Facial and Electrodermal Activity, CEUR Workshop Proc. Jul. 2018; 2142: 208-211.

Xu et al., Exploring Multidimensional Measurements for Pain Evaluation using Facial Action Units, 2020 15th IEEE International Conference on Automatic Face and Gesture Recognition, 2020.

Yan et al., FENP: a Database of Neonatal Facial Expression for Pain Analysis, IEEE Transactions on Affective Computing, 2020.

Zamzmi et al., A Review of Automated Pain Assessment in Infants: Features, Classification Tasks, and Databases, IEEE Reviews in Biomedical Engineering, vol. 11, 2018.

Zeng et al., PIC, a paediatric-specific intensive care database, Scientific Data, 7:14, 2020.

Zhi et al., A comprehensive survey on automatic facial action unit analysis, the Visual Computer (2020) 36:1067-1093.

International Search Report and Written Opinion issued for International Application No. PCT/US19/28277 dated Jul. 15, 2019.

Hazelhoff et al., Behavioral state detection of newborns based on facial expression analysis, International Conference on Advanced Concepts for Intelligent Vision Systems. Springer, Berlin, Heidelberg, 2009.

Holsti et al., Body movements: an important additional factor in discriminating pain from stress in preterm infants, the Clinical journal of pain 2005; 21(6): 491-498.

Lu et al., Facial expression recognition for neonatal pain assessment, 2008 International Conference on Neural Networks and Signal Processing. IEEE, Jun. 8-10, 2008.

Arif-Rahu et al., Bio behavioral measures for pain in the pediatric patient. Pain Management Nursing 13.3 (2012): pp. 157-168.

Bagnato et al. Robust infants face tracking using active appearance models: a mixed-state CONDENSATION approach. Advances in Visual Computing. Springer Berlin Heidelberg, 2007. pp. 13-23.

Beauchemin et al., The computation of optical flow. ACM Computing Surveys (CSUR) vol. 27, No. 3 (1995): pp. 433-466.

Brahnam et al., Introduction to neonatal facial pain detection using common and advanced face classification techniques. Advanced Computational Intelligence Paradigms in Healthcare-1. Springer Berlin Heidelberg, 2007. pp. 225-253.

Brahnam, et al., Machine assessment of neonatal facial expressions of acute pain. Decision Support Systems vol. 43, No. 4 (2007): pp. 1242-1254.

Brahnam et al., Machine recognition and representation of neonatal facial displays of acute pain. Artificial intelligence in medicine vol. 36, No. 3 (2006): pp. 211-222.

Craig, K.D., et al., Pain in the preterm neonate: behavioural and physiological indices. Pain, 1993. vol. 52, No. (3): pp. 287-299.

Fournier-Charrière et al., EVENDOL, a new behavioral pain scale for children ages 0 to 7years in the emergency department: Design and validation. PAIN® vol. 153, No. 8 (2012): pp. 1573-1582.

Gholami et al., Agitation and pain assessment using digital imaging. Engineering in Medicine and Biology Society, 2009. EMBC 2009. Annual International Conference of the IEEE, 2009, pp. 1-13.

Hall et al., The WEKA data mining software: an update. ACM SIGKDD explorations newsletter vol. 11, No. 1, (2009): pp. 1-10.

Hammal et al., Automatic detection of pain intensity. Proceedings of the 14th ACM international conference on Multimodal interaction. ACM, 2012, pp. 1-6.

Hicks et al., The Faces Pain Scale-Revised: toward a common metric in pediatric pain measurement. Pain vol. 93, No. 2 (2001): pp. 173-183.

Holsti et al., Specific Newborn Individualized Developmental Care and Assessment Program movements are associated with acute pain in preterm infants in the neonatal intensive care unit. Pediatrics, 2004. vol. 114, No. 1: pp. 65-72.

Hummel, P.A., et al., Clinical reliability and validity of the N-PASS: neonatal pain, agitation and sedation scale with prolonged pain. Journal of perinatology, 2003. vol. 28, No. 1, pp. 55-60.

(56) References Cited

OTHER PUBLICATIONS

Johnston et al., Experience in a neonatal intensive care unit affects pain response. Pediatrics vol. 98, No. 5 (1996): pp. 925-930.
Kohavi, A study of cross-validation and bootstrap for accuracy estimation and model selection. IJCAI, vol. 14. No. 2. 1995, pp. 1-8.
Lienhart et al., An Extended Set of Haar-like Features for Rapid Object Detection. IEEE ICIP 2002, vol. 1, pp. 900-903, Sep. 2002.
Lindh et al., Heel lancing in term new-born infants: an evaluation of pain by frequency domain analysis of heart rate variability. Pain vol. 80, No. 1 (1999): pp. 143-148.
Nanni et al., A local approach based on a Local Binary Patterns variant texture descriptor for classifying pain states. Expert Systems with Applications vol. 37, No. 12 (2010): pp. 7888-7894.
Saragih et al., Face alignment through subspace constrained mean-shifts. In International Conference of Computer Vision, Sep. 2009, pp. 1-8.
Shreve et al., Automatic Expression Spotting in Videos, Image and Vision Computing, vol. 32, No. 8, pp. 476-486, 2014.
Shreve et al., Macro- and micro-expression spotting in long videos using spatio-temporal strain. International Conference on Automatic Face and Gesture Recognition, pp. 51-56, c 2012 IEEE, Mar. 2011.
Shreve et al., Towards macro- and micro-expressions spotting in videos using strain patterns. Workshop on Applications of Computer Vision, Dec. 2009, pp. 1-6.
Valeri et al., Pain in preterm infants: Effects of sex, gestational age, and neonatal illness severity. Psychology & Neuroscience. vol. 5, No. 1, pp. 11-19.
Viola et al., Rapid Object Detection using a Boosted Cascade of Simple Features. IEEE CVPR, 2001, pp. 1-511-1-518.
Viola et al., Robust real-time face detection. International journal of computer vision vol. 57, No. 2, (2004): pp. 137-154.
Wilson et al., Facial feature detection using Haar classifiers. Journal of Computing Sciences in Colleges vol. 21, No. 4 (2006): pp. 127-133.
Evans et al., Longitudinal comparison of preterm pain responses to repeated heelsticks. Pediatric nursing, 2005. vol. 31, No. 3: pp. 216-221.
Fotiadou et al., Video-based facial discomfort analysis for infants, Proc. SPIE 9029, Visual Information Processing and Communication V, 90290F, 2014, pp. 1-14.
Gibbins, S., et al., Comparison of pain responses in infants of different gestational ages. Neonatology, 2008. vol. 93, No. 1: pp. 10-18.
Hudson-Barr et al., Validation of the pain assessment in neonates (PAIN) scale with the neonatal infant pain scale (NIPS). Neonatal Network. vol. 21, No. 6: pp. 15-21.

Petroni, Marco, et al. Identification of pain from infant cry vocalizations using artificial neural networks (ANNs). SPIE's 1995 Symposium on OE/Aerospace Sensing and Dual Use Photonics. International Society for Optics and Photonics, vol. 2492, pp. 729-737.
Brahnam et al., Neonatal Facial Pain Detection Using NNSOA and LSVM. Ipcv. 2008, pp. 1-7.
Anand, Consensus statement for the prevention and management of pain in the newborn. Archives of pediatrics & adolescent medicine vol. 155, No. 2, (2001): pp. 173-180.
Allegaert et al., Variability in pain expression characteristics in former preterm infants, J. Perinat. Med. vol. 33, No. 5, (2005) pp. 442-448.
Hummel et al., N-PASS: Neonatal Pain, Agitation and Sedation Scale—Reliability and Validity, Poster presented at: the Pediatric Academic Societies annual meeting, Pediatrics/Neonatology, Loyola University Medical Center, Maywood, IL Perinatal Center, Oncology Institute, vol. 2, N. 6, Nov. 2004, pp. 1-4.
Lawrence, The development of a tool to assess neonatal pain. Neonatal network: NN vol. 12, No. 6, (1993): pp. 59-66.
Awais et al., Can pre-trained convolutional neural networks be directly used as a feature extractor for video-based neonatal sleep and wake classification? BMC Res Notes (2020) 13:507.
Awais et al., Novel Framework: Face Feature Selection Algorithm for Neonatal Facial and Related Attributes Recognition, IEEE Access, vol. 8, 59100-59113, Mar. 2020.
Brahnam et al., Neonatal pain detection in videos using the iCOPEvid dataset and an ensemble of descriptors extracted from Gaussian of Local Descriptors, Applied Computing and Informatics, Emerald Insight, May 2019, https://www.emerald.com/insight/2210-8327.htm.
Celona et al., Neonatal Facial Pain Assessment Combining Hand-Crafted and Deep Features, ICIAP 2017 International Workshops, LNCS 10590, pp. 197-204, 2017.
Celona et al., Getting the most of few data for neonatal pain assessment,Pervasive Health '19, May 20-23, 2019, Trento, Italy, pp. 298-301.
Egede et al., Automatic Neonatal Pain Estimation: an Acute Pain in Neonates Database, 2019 8th International Conference on Affective Computing and Intelligent Interaction (ACII), pp. 475-481. IEEE, 2019.
Hammal et al., Automatic Action Unit Detection in Infants Using Convolutional Neural Network, 2017 Seventh International Conference on Affective Computing and Intelligent Interaction (ACII), pp. 216-221. IEEE, 2017.
Homutov et al., Device for Pain Syndrome Study, 2020 International Conference on Industrial Engineering, Applications and Manufacturing (ICIEAM), May 18-22, 2020.

\* cited by examiner

NEONATAL PAIN IDENTIFICATION FROM NEONATAL FACIAL EXPRESSIONS

CROSS-REFERENCE TO RELATED APPLICATIONS

This application is a continuation of and claims priority to PCT International Application No. PCT/US2019/028277, with the same title, filed Apr. 19, 2019, which claims priority to U.S. Provisional Patent Application No. 62/660,072, entitled "A Comprehensive and Context-Sensitive Neonatal Pain Assessment Using Computer Vision," filed Apr. 19, 2018 and to U.S. Provisional Patent Application No. 62/660,038, entitled "Neonatal Convolutional Neural Network (N-CNN) for Pain Assessment Based on Facial Expression," filed Apr. 19, 2018, the entirety of each is incorporated herein by reference.

BACKGROUND OF THE INVENTION

1. Field of the Invention

This invention relates, generally, to a system and method for use in identifying the existence of pain in a neonatal patient. More specifically, it relates to a system and method of assessing neonatal pain based on a series of facial expressions.

2. Brief Description of the Prior Art

Infants receiving care in the Neonatal Intensive Care Unit (NICU) might experience several painful procedures during their stay. Several pediatric studies have reported several long-term outcomes of repeated pain exposure in early life. Examples of these outcomes include delayed visual-perceptual development, lower IQ, a higher risk of internalizing behavior and alterations in brain structure and function.

The realization of the adverse outcomes associated with neonatal pain exposure has led to the increased use of opioids such as Fentanyl and Morphine, as treatment for neonatal pain. While analgesic medications can reduce the consequences of neonatal pain exposure, recent studies have found several short-term and long-term side effects related to the use of such medications.

These findings suggest that the failure to treat pain when needed (i.e., under treatment) as well as the administration of analgesic medications in the absence of pain (i.e., over treatment) can cause serious outcomes and permanently alter brain structure and structure.

Caregivers assess neonatal pain by observing behavioral (e.g., facial expression and crying) and physiological (e.g., vital signs changes) indicators using multidimensional pain scales such as NIPS (Neonatal Infant Pain Scale), FLACC (Face, Legs, Activity, Crying, and Consolability), and NFCS (Neonatal Facial Coding System).

This practice is inconsistent because it depends highly on the observer bias. Additionally, it is discontinuous and requires a large number of well-trained nurses to ensure proper utilization of the tools. The discontinuous nature of the current practice, as well as the inter-rater variations, may result in delayed intervention and inconsistent treatment of pain.

Accordingly, what is needed is an automated and continuous tool that generates prompt and consistent assessment of neonatal pain. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

In various embodiments, the present invention provides an automated system that can decrease the caregiver's burden of observation and documentation while providing continuous monitoring of a neonatal patient. The automated system of the present invention monitors facial movements associated with pain in neonates, including but not limited to, deepening of the nasolabial furrow, brow lowering, narrowed eyes, vertical and horizontal mouth stretch, lip pursing, lip opening, tongue protrusion, taut tongue and chin quiver. The automatic recognition of pain facial expression consists of three main stages: (1) face detection and registration; (2) feature extraction; and (3) pain expression recognition.

In a particular embodiment, a computer-implemented method for identifying when a neonate of interest is experiencing pain is provided. The method includes, training a neonatal convolutional neural network (N-CNN) using a neonatal pain assessment database, the neonatal pain assessment database (NPAD) comprising image data of a plurality of neonate faces acquired under a pain condition and image data of a plurality of neonate faces acquired under a no-pain condition, to establish a trained N-CNN. The method further includes, monitoring a face of a neonate of interest with a video image capture device to capture image data of the face of a neonate of interest, applying the trained N-CNN to the image data captured by the video image capture device to determine if the neonate of interest is experiencing a pain condition or a no-pain condition and providing an output from the N-CNN indicating whether the neonate of interest is experiencing a pain condition or a no-pain condition.

The method may further include preprocessing the image data of the neonate of interest to generate a plurality of preprocessed frames focused on the face of the neonate of interest. The method further includes, performing a combination of convolution and max pooling of the preprocessed frames at a right branch, a left branch and a central branch of the N-CNN, merging results from the right branch, the left branch and the central branch to generate merged results and performing a combination of convolution and max pooling of the merged results to determine if the neonate of interest is experiencing a pain condition or a no-pain condition.

In another embodiment, the present invention provides a system for identifying a pain condition in a neonate of interest. The system includes, an image data interface connectable to receive image data comprising a face of a neonate of interest and processing circuitry configured as a cascaded Neonatal Convolutional Neural Network (N-CNN) connected to receive and process the image data and to determine whether the neonate of interest is experiencing a pain condition or a no-pain condition, wherein the cascaded N-CNN is trained using a neonatal pain assessment database (NPAD) comprising image data of a plurality of neonate faces acquired under a pain condition and image data of a plurality of neonate faces acquired under a no-pain condition. System may further include, a video image capture device coupled to the image data interface and an output interface configured to provide the determination whether the neonate of interest is experiencing a pain condition or a no-pain condition to a user.

In an additional embodiment, the present invention provides a non-transitory computer readable storage media having computer-executable instructions, when executed by a processor for, training a neonatal convolutional neural network (N-CNN) using a neonatal pain assessment database, the neonatal pain assessment database (NPAD) comprising image data of a plurality of neonate faces acquired under a pain condition and image data of a plurality of neonate faces acquired under a no-pain condition. The instructions, when executed by a processor further include establishing a trained N-CNN, monitoring a face of a neonate of interest with a video image capture device to capture image data of the face of a neonate of interest for and applying the trained N-CNN to the image data captured by the video image capture device to determine if the neonate of interest is experiencing a pain condition or a no-pain condition and for providing an output from the N-CNN indicating whether the neonate of interest is experiencing a pain condition or a no-pain condition.

Accordingly, in various embodiments, the present invention provides a system and method for an automated and continuous tool that generates prompt and consistent assessment of neonatal pain.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
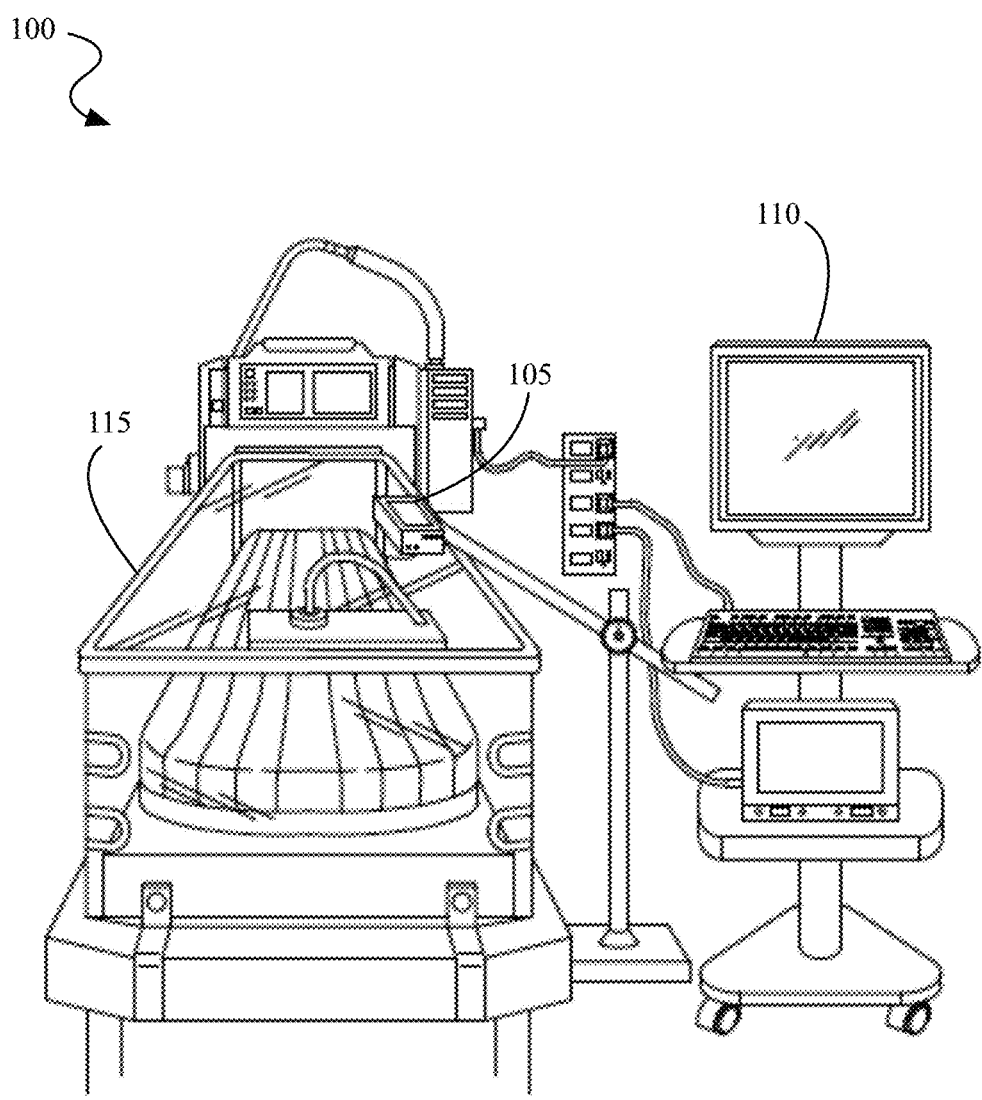
FIG. 1 is an image illustrating an exemplary setup for image data collection of a neonate of interest.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The recent innovations in computer vision facilitated the development of automated approaches that continuously and consistently monitor pain and provide consistent assessment. Various methods were proposed to automatically assess pain using behavioral (e.g., facial expression and crying) or physiological (e.g., changes in vital signs and cerebral hemodynamic changes) indicators.

The vast majority of these existing methods asses and estimate pain based on analysis of facial expression. This focus might be attributed to the fact that facial expression is the most common and specific indicator of pain. As such, most pain scales include facial expression as a main indicator for pain assessment. Of the existing methods for automatic pain expression analysis, only a few methods focused on neonatal pain due to the lack of publicly-available neonatal databases. Another reason might be the belief that the algorithms designed for adults should have similar performance when applied to neonates. Contrary to this teaching, it is believed that the methods designed for assessing adults' pain will not have similar performance and might completely fail because the facial morphology and movements dynamics vary between infants and adults. In addition, infants' facial expressions include additional movements and units that are not present in the Facial Action Coding System (FACS). Therefore, Neonatal FACS was introduced as an extension of FACS.

The automatic methods of neonatal pain expression recognition can be divided into two main categories: handcrafted based methods and deep learning based methods.

Handcrafted based methods extract important features from a given signal using certain predefined algorithms designed by experts. The extracted features are then used with the traditional machine learning classifiers (e.g., Support Vector Machines) for emotion recognition. Several handcrafted based methods have been introduced to detect and classify pain expression of neonates. In one handcrafted method, a COPE (Classification of Pain Expression) database, which consists of 204 color images captured for 26 neonates while experiencing pain and no-pain stimuli was utilized. The method takes a static image as input and concatenates it into a feature vector of $\text{Image}_w \times \text{Image}_H$ dimensions with values ranging from 0 to 255. Then, Principal Component Analysis (PCA) was applied to reduce the vector's dimensionality. For classification, distance-based classifiers and Support Vector Machines (SVMs) were used to classify the images into pain or no-pain. The results showed that SVMs evaluated using 10-fold cross-validation achieved the best recognition rate and outperformed distance-based classifiers in classifying pain versus no-pain (88.00%). Presentations of other handcrafted based methods, such as Local Binary Pattern (LBP), Geometric-based Features, Histogram of Oriented Gradients (HOG), Active Appearance Model (AAM), and Optical Strain (OS) for assessing neonatal pain can be found in the art.

Recently, deep features extracted by Convolutional Neural Networks (CNNs) showed good performance in several classification tasks. The main difference between handcrafted features and deep features is that the features extracted by CNN are learned, at multiple levels of abstraction, directly from the data, whereas the handcrafted features are designed beforehand by human experts to extract a given set of chosen characteristics. Deep features extracted from static images of COPE database to classify these images into pain or no-pain images. Particularly, the presented method extracted deep features using a pre-trained CNN architecture known as VGG-Face. In addition to VGG-Face, MBPCNN model, which uses a mapped LBP (Local Binary Patterns) features as input to a VGG-S CNN architecture, was used for feature extraction. To generate the feature vector for classification, the last two fully connected layers and the softmax layer of both CNNs (i.e., VGG-Face and MBPCNN) were removed. The length of the extracted feature vector is 4096. The extracted feature vectors were then used to train Support Vector Machine. Testing the trained model on unseen data (i.e., leave-one-subject-out cross validation) achieved 82.42%, 81.53%, and 83.78% for VGG-Face, MBPCNN, and VGG-Face+MBPCNN, respectively.

In view of the short-comings in the current state of the art, in various embodiments, the present invention provides a Neonatal Convolutional Neural Network (N-CNN) designed and trained from scratch to recognize neonatal pain. To the best of our knowledge, this is the first CNN that has been designed and built for recognizing neonatal pain emotion. The proposed N-CNN outperformed existing methods of neonatal pain assessment and proved the feasibility of automatic pain assessment in typical neonatal care environments.

As shown in FIG. 1, a system 100 for identifying a pain condition in a neonate of interest may include a video image capture device 105 for capturing real-time video data of a neonate in an incubator 115, or alternatively a crib or bed, and a monitoring device 110. The video image capture device 105 would be place above the neonate in the incubator 115 in a manner to allow for the capture of facial expressions from the neonate.

In some embodiments the video image capture device 105 may be a GoPro Hero4+ video camera which can be used to record video and audio signals. The camera may be triggered remotely using a GoPro application installed on a smartphone or alternatively on the monitoring device 110. The capture image data includes the infant's face, head, and body as well as the sounds of neonates and background noise (e.g., sounds of equipment and nurses).

In an exemplary embodiment, neonates (N=31 neonates, 15 females and 16 males) were recorded while undergoing a brief acute stimulus (e.g., heel lancing or immunization) during their hospitalization in the NICU at a local Hospital. Infants' average gestational age was 35.9, ranging from 30.4 to 40.6. The ethnic distribution was 17% Caucasian, 47% White, 17% African American, 12% Asian, and 7% other. Any infant born in the range of 28 and 41 gestation weeks was eligible for enrollment after obtaining an informed consent from the parents. Infants with cranial facial abnormalities were excluded.

In this exemplary embodiment, a GoPro® camera was used to record infants' facial expression, body movement, and crying sound. All the recordings were carried out in the normal clinical environment (unconstrained environment) that was only modified by the addition of the camera.

Data was collected for each infant during eight time periods: 1) prior to the painful procedure to get a baseline state; 2) procedure preparation period that begins with first touch, may include positioning or skin preparation, and ends with skin breaking; 3) painful procedure period, which lasts for the duration of the procedure; 4) one minute post completion of the painful procedure; 5) two minutes post completion; 6) three minutes post completion; and 7) four minutes post completion; 8) recovery period five minutes post procedure. Each time period was observed by trained nurses to provide manual pain assessment using NIPS (Neonatal Infant Pain Scale). Cohen's kappa coefficient was used to measure agreements between the nurses (k=0.85) and excluded instances of disagreement.

NIPS scale consists of facial expression, crying, body movement (i.e., arms and legs), state of arousal, and physiological readings (e.g., breathing pattern). Each element of NIPS was manually scored on a scale of 0-1 with the exception of cry, which was scored on a scale of 0-1-2. A total score >4 indicates severe pain, a score of 3-4 indicates moderate pain, and a score of 0-2 indicates no-pain. To get the ground truth for each video epoch, we used the thresholding of the total score (i.e., severe pain, moderate pain, or no pain) as the ground truth labels. In this embodiment of the invention, only pain and no-pain labels were included. Moderate pain labels were excluded because the number of epochs for moderate pain is small in the current database. It is noted that all the data were collected during routine clinical procedures and carried out in the normal clinical environment that is only modified by the addition of the cameras. This makes the Neonatal Pain Assessment Database (NPAD) of the present invention more challenging and representative of the real-world condition. A portion of this database will be made available, via a web-accessible interface, for research in neonatal pain assessment.

The proposed pain assessment system consists of two main stages: 1) preprocessing of the visual signals and 2) pain recognition using N-CNN. In the first stage ZFace face tracker was applied in each video's frame to detect the face and obtain 49 facial landmark points. The tracker outputs the coordinates of these points as well as a failure message to indicate the failure frames. The points of failure frames were annotated manually for further analysis. For each frame, the detected points were used to register and crop the infant's exact face region. Then, the key frames were selected from each video, thereby removing many similar frames, which were then used as input to the N-CNN. The total number of the key frames obtained from all videos was 3026 frames. Note that all the extracted frames are RGB images. All the extracted frames were then re-sized to 120×120 using a bi-cubic interpolation method.

ZFace is face tracking software that registers a dense 3D shape in real time for each frame of the video using a single 2D image of a person's face. The use of Zface in this embodiment is not intended to be limiting and other face tracking applications are within the scope of the present invention.

Since the total number of frames is too small to train a CNN end-to-end, data augmentation was performed on the training set (50%—1513 frames), wherein each frame was randomly rotated by 30 degrees to generate a total of 12 images for each frame. Each rotated image was then flipped horizontally and vertically, thereby generating a total of 36 (12 original+12 horizontal-flip+12 vertical-flip) augmented images for each frame. This procedure provides a total of 54,468 augmented images. Note that no data augmentation was performed on the separated testing set of 1513 frames. In this exemplary embodiment, Keras was used for image augmentation. Keras is a known software algorithm that applies a transformation to an image according to given parameters. However, this is not intended to be limiting and other image augmentations methods are within the scope of the present invention.

Figure 2:
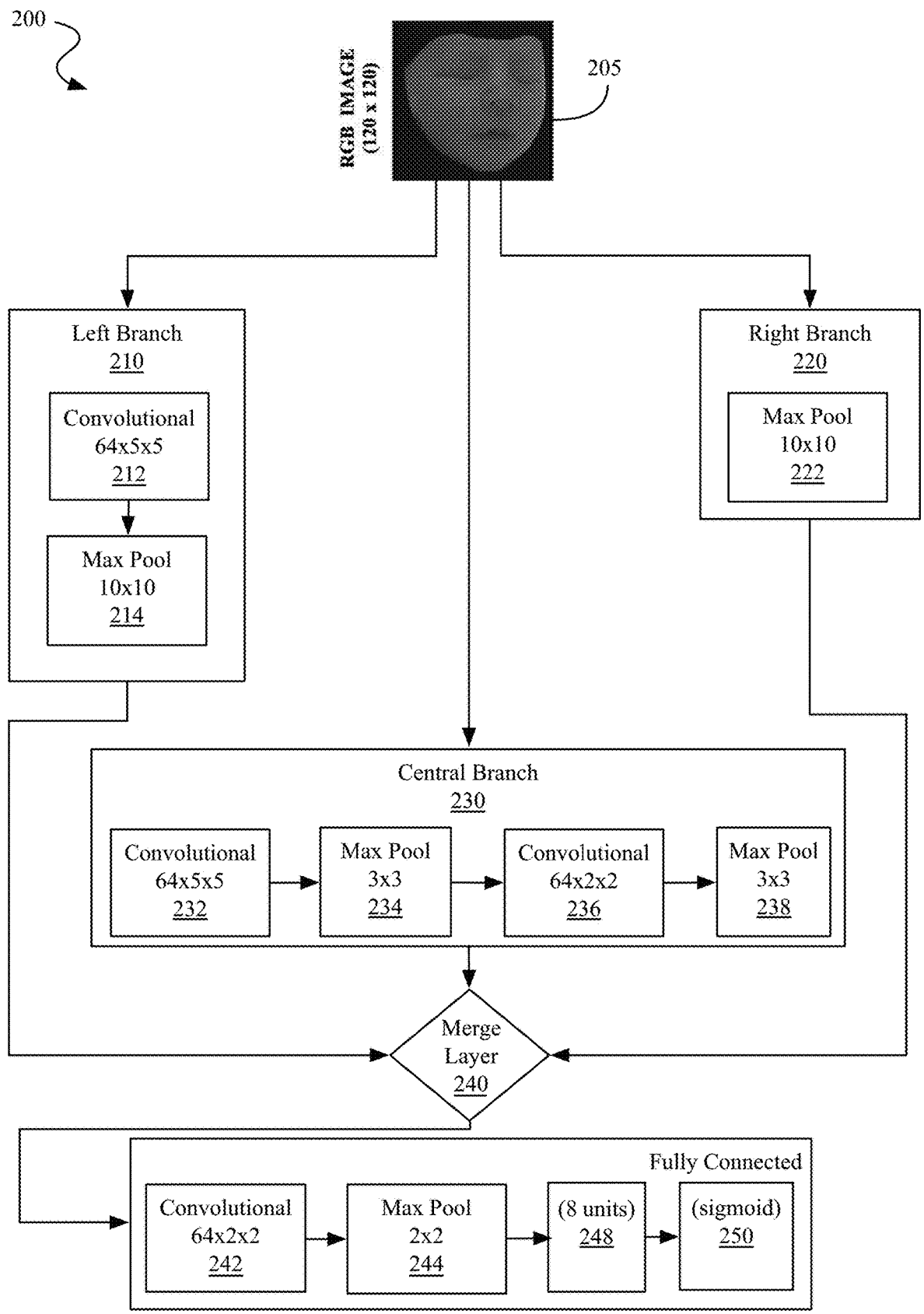
FIG. 2 is a flow diagram illustrating the architecture of the cascaded N-CNN for pain identification in neonates, in accordance with an embodiment of the present invention.

With reference to FIG. 2, the proposed Neonatal Convolutional Neural Network (N-CNN) 200, is a cascaded CNN that has three main branches. Each of these branches performs a specific task and captures a different set of features from the RGB images 205 provided. For example, the right branch 220 down-samples the image size and captures the most prominent features, whereas the left branch 210 captures more generic convolutional features such as the image's texture and color blobs. The central branch 230 extracts deeper features from the image since it has four layers. After feeding the image 205 into these three branches 210, 220, 230, the outputs of the three branches are merged 240 by concatenation.

In a particular embodiment, the right branch 220 consists of a pooling layer that performs max pooling operation using 10×10 filter 222. The central branch 230 consists of two convolutions layers 232, 236 with 64 filters of size 5×5 followed by pooling layers 234, 238 with 3×3 filter (i.e., conv1→pool1→conv2→pool2). The left branch 210 consists of two layers, a convolutional layer 212 with 64 filters of size 5×5 and a pooling layer 214 to perform max pooling operation using 10×10 filter. This cascaded architecture allows for the combination of specific information for each image (right branch 220) with the generic information (edges and blobs from left branch 210) generated after applying convolutions.

After merging 240 the generic features with image-specific features, another convolution layer 242 with 64 filters of size 2×2 followed by a max pooling layer 244 with 2×2 filters is added, to maintain the generic information of the image and provide more features, resulting in fully connected 8 units 248 and fully connected sigmoid 250. The complete set of N-CNN parameters is presented in Table I. The results indicate that the proposed cascaded CNN architecture has much better classification performance than the regular CNN architecture.

TABLE I

PARAMETERS OF N-CNN

RIGHT BRANCH

Input Image: 120 × 120 × 3
Max-pool 1: 10 × 10, st. 10, pad 0

CENTRAL BRANCH

Input Image: 120 × 120 × 3
Conv 1: 64 × 5 × 5, st. 1, pad 0
Leaky ReLU; 0.01
Max-pool 2: 3 × 3, st. 3, pad 0
Conv 2: 64 × 2 × 2, st. 1, pad 0
Leaky ReLU: 0.01
Max-pool 3: 3 × 3, st. 3, pad 0
Dropout: 0.1

LEFT BRANCH

Input Image: 120 × 120 × 3
Conv 3: 64 × 5 × 5, st. 1, pad 0
Leaky ReLU: 0.01
Max-pool 4: 10 × 10, st. 10, pad 0
Dropout: 0.1

MERGE LAYER

RIGHT, CENTRAL, and LEFT
Conv 4 + ReLU: 64 × 2 × 2, st. 1, pad 0
Max-pool 5: 2 × 2, st. 2, pad 0
Fully Connected 1 + ReLU: 8
L2 Regularizer , Dropout: 0.01, 0.1
Fully Connected 2 + sigmoid: 1

The N-CNN of the present invention was trained from scratch with random weights initialization and 72593 training parameters. The total number of epochs for training was 100. RMSprop (Root Mean Square Propagation) was used as a gradient descent optimization algorithm and a constant learning rate of 0.0001. A batch size of 16 was used for both training and validating N-CNN. It is noted that while experiments were performed with different batch sizes (8/16/24/32/40), a batch size of 16 was chosen because it achieved the best performance. An L2 regularizer and dropout as applied before the final classification layer to prevent over-fitting. The entire dataset was randomly divided into equal training set (1513 frames) and testing set (remaining 1513 frames). The training set (1513 frames) was further divided randomly into final-training (70%), validation (20%) and test (10%). Image augmentation was performed in the training set as previously described and Keras and Tensorflow backend were used for training and testing the N-CNN.

The performance of neonatal pain assessment using the N-CNN architecture of the present invention was evaluated. The network was trained and tested using the NPAD dataset. The performance was reported using the accuracy and area under the Receiver Operating Characteristic curve (AUC). The accuracy and AUC were computed by averaging the performance of three testing sets: 1) Randomly splitting the database (3026 images) into nonoverlapped training and testing sets three times to obtain three training sets (TR1-TR3) and testing sets (TS1-TS3). 2) Using each training set to train the CNN followed by evaluating on its corresponding testing set (e.g., TR1 for training and TS1 for testing), wherein all the subjects in the training set were different from the subjects included in the testing set. 3) Averaging the accuracies and the AUC values of the three testing sets.

As shown in Table II, using N-CNN architecture for neonatal pain assessment achieved 91.00% accuracy and 0.93 AUC. The last four columns of Table II present the True Positive Rate (TPR), True Negative Rate (TNR), False Positive Rate (FPR), and False Negative Rate (FNR), respectively. It is believed that FPR is lower than FNR because the number of pain instances is smaller than the no-pain instances. It is worth mentioning that minimizing both the FPR and FNR rates is equally important in case of pain assessment as pediatric studies reported serious outcomes of both over-treatment (FPR) and under-treatment (FNR).

TABLE II

ASSESSMENT BASED ON FACE EXPRESSION (NPAD DATASET)

|  | Accuracy | AUC | TPR | TNR | FPR | FNR |
|---|---|---|---|---|---|---|
| N-CNN | 91.0% | 0.93 | 82.9% | 93.5% | 6.5% | 17.1% |
| ResNet | 87.1% | 0.90 | 79.9% | 89.2% | 10.8% | 20.0% |
| LBP | 87.66% | 0.84 | 79.5% | 92.3% | 7.7% | 20.5% |

In addition to NPAD dataset, the performance of N-CNN was evaluated on another neonatal dataset (COPE). COPE is a known data set of neonates that is currently available for research use. Additionally, iCOPE (Infant Classification of Pain Expressions) is another recently available data set of neonate expressions that could be utilized to further evaluate the performance of N-CNN.

The trained network was applied on static images of the COPE dataset the results were reported. COPE dataset consists of 204 static images taken during four different stimuli: 1) Pain stimulus during the heel lancing. 2) Rest/cry stimulus during the transportation of an infant from one crib to another (rest images and cry images). 3) Air stimulus to the nose. 4) Friction stimulus, which involves receiving friction on the external lateral surface of the heel with cotton soaked in alcohol.

The COPE images were divided into two sets: no-pain set and pain set. The pain set contained images of neonates during acute painful stimulus (heel-lancing) while the no-pain set contains images of neonates during the other three stimuli. Table III presents the performance of evaluating N-CNN on the COPE dataset. As shown in the table, N-CNN with COPE dataset achieved 84.5% average accuracy. It is believed that the lower accuracy of applying N-CNN to COPE, in comparison with the accuracy of applying N-CNN to the NPAD database, is attributed to the difference between COPE and the NPAD database of the present invention. The NPAD neonatal database consists of pain (heel lancing) and no-pain (normal or rest states) while COPE database was divided into pain set (heel lancing) and no-pain set (rest/cry, air, and friction).

TABLE III

ASSESSMENT BASED ON FACE EXPRESSION (COPE DATASET)

|  | Accuracy | TPR | TNR | FPR | FNR |
|---|---|---|---|---|---|
| N-CNN | 84.5% | 79.2% | 89.6% | 10.4% | 20.8% |
| ResNet | 82.87% | 77.78% | 87% | 13% | 22.22% |
| LBP | 81.3% | 76.6% | 88.9% | 11.1% | 23.4% |

ResNet, which stands for Residual network, is one of the most groundbreaking networks in the deep learning community. Several works have reported the excellent performance of this network in different classification tasks. In an embodiment of the present invention, the ResNet50 architecture was used to perform pain classification. Specifically, the ResNet50 architecture was re-trained using the NPAD dataset of the present invention as follows. First, the number of classes in the classification layer was changed from 1000 to binary and then a sigmoid activation function was utilized for classification. The tuned ResNet CNN was trained using the same batch size (16) and learning rate (0.0001) with RMSPROP gradient descent algorithm. Before training the network, augmentation was performed on the training set as previously described. The NPAD dataset was randomly split into training and testing three times as previously discussed. The re-trained ResNet50 architecture achieved 87.1% accuracy with 0.90 AUC. Table III presents the performance of assessing neonatal pain using ResNet50 architecture. As the table shows, N-CNN outperformed ResNet50 in assessing neonatal pain. It is believed that the higher performance of N-CNN can be attributed to the small number of images in the training set (thousands of images) as compared to ResNet50. The N-CNN architecture has a smaller number of parameters (73593 parameters) comparing to ResNet50 architecture (millions of parameters). Because the vast majority of medical data sets are small in size, N-CNN can be more suitable for medical applications.

Applying the retrained ResNet50 architecture on COPE dataset was also evaluated and the results are reported in Table III. It is believed that the lower accuracy of applying ResNet50 to COPE, in comparison with the accuracy of applying ResNet50 to NPAD dataset, is attributed to the difference between COPE and NPAD datasets.

The experimental results show comparisons of the performance of neonatal pain assessment using the proposed N-CNN, the re-trained ResNet50 architecture, and a handcrafted method on two neonatal datasets (NPAD and COPE). The proposed N-CNN achieved the highest performance (91.00% average accuracy and 0.93 AUC) in both datasets. The obtained assessment results are encouraging and suggest that the automatic recognition of neonatal pain is feasible and can provide a viable and more efficient alternative to the current standard of pain assessment.

Figure 3:
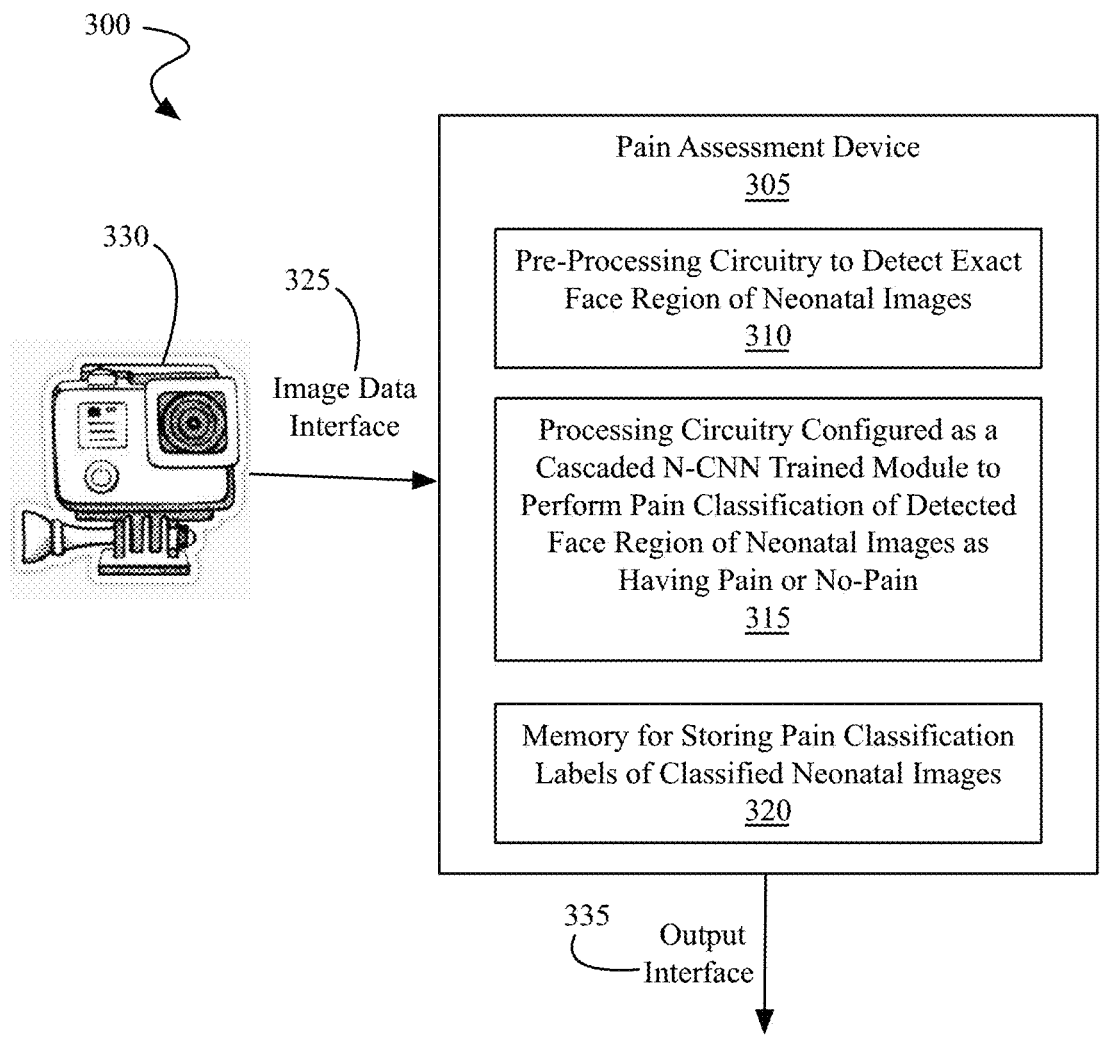
FIG. 3 is a block diagram illustrating the structural components of the neonatal pain identification system, in accordance with an embodiment of the present invention.

FIG. 3 illustrates an exemplary system 300 for automatically identifying neonatal pain conditions based on facial recognition. The system 300 includes a video image capture device 330 and an image data interface 325 in communication with a pain assessment device 305. The pain assessment device 305 may further include pre-processing circuitry to detect the exact face region of neonatal images 310, processing circuitry configured as a cascaded N-CNN trained module to perform pain classification of the detected face region of the neonatal images as having pain or no-pain 315 and memory for storing the pain classification labels of the classified neonatal images 320.

In operation, the processing circuitry configured as a cascaded N-CNN trained module 315 is first trained using the NPAD in preparation for assessing the facial images of neonatal patients. Following the training of the cascaded N-CNN, the pre-processing circuitry 310 is used to detect the exact face region of the neonatal images acquired by the video image capture device 330. The processing circuitry configured as a cascaded N-CNN trained module 315 is then used to perform pain classification of the detected face region of the neonatal images as having pain or no-pain. Following the classification, the memory 320 is used to store the pain classification labels for the neonatal images.

Hardware and Software Infrastructure Examples

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like, scripting languages such as MatLab and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A computer-implemented method for identifying when a neonate of interest is experiencing pain, the method comprising:
    training a neonatal convolutional neural network (N-CNN) using a neonatal pain assessment database (NPAD), the neonatal pain assessment database (NPAD) comprising images of a plurality of neonate faces acquired under a pain condition and images of the plurality of neonate faces acquired under a no-pain condition, to establish a trained N-CNN;
    monitoring a face of the neonate of interest with a video image capture device to capture image data of the face of the neonate of interest;
    applying the trained N-CNN to the image data captured by the video image capture device to determine if the neonate of interest is experiencing the pain condition or the no-pain condition, wherein applying the trained N-CNN to the image data further comprises:
        preprocessing the image data captured by the video image capture device to generate a plurality of preprocessed frames focused on the face of the neonate of interest;
        performing a combination of a convolution layer and a max pooling operation on each of the plurality of preprocessed frames at a right branch of the N-CNN to extract prominent features from the plurality of preprocessed frames, at a left branch of the N-CNN to extract generic features from the plurality of preprocessed frames and at a central branch of the N-CNN to extract deep features from the plurality of preprocessed frames;
        merging the prominent features from the plurality of preprocessed frames extracted at the right branch, the generic features extracted at the left branch and the deep features extracted at the central branch to generate merged results;
        performing a combination of a convolution layer and a max pooling operation of the merged results to determine if the neonate of interest is experiencing the pain condition or the no-pain condition; and
    providing an output from the N-CNN indicating whether the neonate of interest is experiencing the pain condition or the no-pain condition.

2. The method of claim 1, wherein the images of the neonatal pain assessment database (NPAD) comprise:
    a first set of images of the plurality of neonate faces acquired prior to application of the pain condition, as a baseline;
    a second set of images of the plurality of neonate faces acquired during a preparation period prior to the application of the pain condition;
    a third set of images of the plurality of neonate faces acquired during the application of the pain condition;
    a fourth set of images of the plurality of neonate faces acquired one minute post completion of the application of the pain condition;
    a fifth set of images of the plurality of neonate faces acquired two minutes post completion of the application of the pain condition;
    a sixth set of images of the plurality of neonate faces acquired three minutes post completion of the application of the pain condition;

a seventh set of images of the plurality of neonate faces acquired four minutes post completion of the application of the pain condition; and an eighth set of images of the plurality of neonate faces acquired five minutes post completion of the application of the pain condition.

3. The method of claim 2, further comprising using a Neonatal Infant Pain Scale (NIPS) performed by a medical professional to classify each of the acquired first set of images, the acquired second set of images, the acquired third set of images, the acquired fourth set of images, the acquired fifth set of images, the acquired sixth set of images, the acquired seventh set of images and the acquired eight set of images as being acquired under the pain condition or being acquired under the no-pain condition.

4. The method of claim 3, further comprising:

applying a face tracker to each of the plurality of images in each of the first, second, third, fourth, fifth, sixth, seventh and eighth sets of images classified as being acquired under the pain condition and classified as being under the no-pain condition to detect the face of the neonate in each of the plurality of images in each of the first, second, third, fourth, fifth, sixth, seventh and eighth sets of images;

identifying a plurality of facial landmark points on the face of the neonate detected in each of the plurality of images, each of the facial landmark points having an associated set of coordinates;

registering and cropping each of the plurality of images based upon the set of coordinates of the facial landmark points to focus on the face of the neonate detected in each of the plurality of images; and removing any images of the plurality of images that are determined to be the same, thereby establishing the neonatal pain assessment database (NPAD).

5. The method of claim 4, further comprising performing data augmentation to increase a number of images in the neonatal pain assessment database (NPAD) for training the N-CNN.

6. The method of claim 1, wherein preprocessing the image data captured by the video image capture device to generate the plurality of preprocessed frames focused on the face of the neonate of interest further comprises:

applying a face tracker to the image data captured by the video image capture device to detect the face of the neonate of interest in each of a plurality of frames;

identifying a plurality of facial landmark points on the face of the neonate of interest in each of the plurality of frames, each of the facial landmark points having an associated set of coordinates; and registering and cropping each of the plurality of frames based upon the set of coordinates of the facial landmark points to generate the plurality of preprocessed frames focused on the face of the neonate of interest.

7. The method of claim 1, wherein performing the combination of the convolution layer and the max pooling operation on each of the plurality of preprocessed frames at the right branch of the N-CNN to extract the prominent features from the plurality of preprocessed frames, at the left branch of the N-CNN to extract the generic features from the plurality of preprocessed frames and at the central branch of the N-CNN to extract the deep features from the plurality of preprocessed frames further comprises:

performing the max pooling operation on each of the plurality of preprocessed frames using a 10×10 filter in the right branch of the N-CNN to extract the prominent features from the plurality of preprocessed frames;

performing the convolution layer with 64 filters of size 5×5 and performing the max pooling operation using a 3×3 filter, performing another convolution layer with 64 filters of size 5×5 and performing another max pooling operation using the 3×3 filter in the central branch of the N-CNN to extract the generic features from the plurality of preprocessed frames;

performing the convolution layer with 64 filters of size 5×5 and performing the max pooling operation using a 10×10 filter in the left branch of the N-CNN to extract the deep features from the plurality of preprocessed frames; and performing the convolution layer with 64 filters of size 2×2 and the max pooling operation using a 2×2 filter on the merged results to determine if the neonate of interest is experiencing the pain condition or the no-pain condition.

8. A system for identifying a pain condition in a neonate of interest, the system comprising:

an image data interface connectable to receive image data comprising a face of the neonate of interest;

processing circuitry configured as a cascaded Neonatal Convolutional Neural Network (N-CNN) connected to receive and process the image data and to determine whether the neonate of interest is experiencing a pain condition or a no-pain condition, wherein the cascaded N-CNN is trained using a neonatal pain assessment database (NPAD) comprising images of a plurality of neonate faces acquired under the pain condition and images of the plurality of neonate faces acquired under the no-pain condition, and wherein the trained cascaded N-CNN is further configured to:

preprocess the image data comprising the face of the neonate of interest to generate a plurality of preprocessed frames focused on the face of the neonate of interest;

perform a combination of a convolution layer and a max pooling operation of the plurality of preprocessed frames at a right branch of the N-CNN to extract prominent features from the plurality of preprocessed frames, at a left branch of the N-CNN to extract generic features from the plurality of preprocessed frames and at a central branch of the N-CNN to extract deep features from the plurality of preprocessed frames;

merging the prominent features from the plurality of preprocessed frames extracted at the right branch, the generic features extracted at the left branch and the deep features extracted at the central branch to generate merged results; and perform a combination of a convolution layer and a max pooling operation of the merged results to determine if the neonate of interest is experiencing the pain condition or the no-pain condition.

9. The system of claim 8, further comprising: a video image capture device coupled to the image data interface, the video image capture device for monitoring the face of the neonate of interest to capture the image data comprising the face of the neonate of interest.

10. The system of claim 9, wherein the trained cascaded N-CNN is further configured to preprocess the image data comprising the face of the neonate of interest captured by the video capture device by: applying a face tracker to the image data comprising the face of the neonate of interest captured by the video camera to detect the face of the neonate of interest in each of a plurality of frames, identifying a plurality of facial landmark points on the face of the neonate of interest in each of the plurality of frames, each of the facial landmark points having an associated set of coordinates and registering and cropping each of the plurality of frames based upon the set of coordinates of the facial landmark points to generate the plurality of preprocessed frames focused on the face of the neonate of interest.

11. The system of claim 10, wherein the trained cascaded N-CNN is further configured to identify whether the neonate of interest is experiencing the pain condition or the no-pain condition by: performing the max pooling operation on each of the plurality of preprocessed frames in the right branch of the N-CNN using a 10×10 filter to extract the prominent features, performing the convolution layer with 64 filters of size 5×5 and performing the max pooling operation using a 3×3 filter, performing another convolution layer with 64 filters of size 5×5 and performing another max pooling operation using a 3×3 filter in the central branch of the N-CNN to extract the generic features, performing the convolution layer with 64 filters of size 5×5 and performing the max pooling operation using a 10×10 filter in the left branch of the N-CNN to extract the deep features, merging the prominent, generic, and deep features from the right branch, the central branch and the left branch, respectfully, to generate the merged results and performing the combination of the convolution layer with 64 filters of size 2×2 and the max pooling operation using a 2×2 filter on the merged results.

12. The system of claim 8, further comprising: an output interface configured to provide the determination whether the neonate of interest is experiencing the pain condition or the no-pain condition to a user.

13. The system of claim 8, wherein the processing circuitry is further configured as a N-CNN training module and the neonatal pain assessment database (NPAD) is stored in a memory module, the NPAD comprising:
- a first set of images of the plurality of neonate faces acquired prior to application of the pain condition, as a baseline;
- a second set of images of the plurality of neonate faces acquired during a preparation period prior to the application of the pain condition;
- a third set of images of the plurality of neonate faces acquired during the application of the pain condition;
- a fourth set of images of the plurality of neonate faces acquired one minute post completion of the application of the pain condition;
- a fifth set of images of the plurality of neonate faces acquired two minutes post completion of the application of the pain condition;
- a sixth set of images of the plurality of neonate faces acquired three minutes post completion of the application of the pain condition;
- a seventh set of images of the plurality of neonate faces acquired four minutes post completion of the application of the pain condition; and
- an eighth set of images of the plurality of neonate faces acquired five minutes post completion of the application of the pain condition.

14. The system of claim 13, wherein the N-CNN training module is further configured for using a Neonatal Infant Pain Scale (NIPS) performed by a medical professional to classify each of the acquired first set of images, the acquired second set of images, the acquired third set of images, the acquired fourth set of images, the acquired fifth set of images, the acquired sixth set of images, the acquired seventh set of images and the acquired eight set of images of the plurality of neonate faces as being acquired under the pain condition or being acquired under the no-pain condition.

15. The system of claim 14, wherein the N-CNN training module is further configured for:
- applying a face tracker to each of the plurality of images in each of the first, second, third, fourth, fifth, sixth, seventh and eighth sets of images classified as being acquired under the pain condition and classified as being under the no-pain condition to detect the face of the neonate in each of the plurality of images in each of the first, second, third, fourth, fifth, sixth, seventh and eighth set of images;
- identifying a plurality of facial landmark points on the face of the neonate detected in each of the plurality of images, each of the facial landmark points having an associated set of coordinates;
- registering and cropping each of the plurality of images based upon the set of coordinates of the facial landmark points to focus on the face of the neonate; and
- removing any images of the plurality of images that are determined to be the same, thereby establishing the neonatal pain assessment database (NPAD).

16. The system of claim 14, wherein the cascaded N-CNN training module is further configured for performing data augmentation to increase a number of images in the neonatal pain assessment database (NPAD).

17. A non-transitory computer readable storage media having computer-executable instructions, when executed by a processor for: training a neonatal convolutional neural network (N-CNN) using a neonatal pain assessment database, the neonatal pain assessment database (NPAD) comprising images of a plurality of neonate faces acquired under a pain condition and images of the plurality of neonate faces acquired under a no-pain condition, to establish a trained N-CNN, monitoring a face of a neonate of interest with a video image capture device to capture image data of the face of the neonate of interest, applying the trained N-CNN to the image data captured by the video image capture device to determine if the neonate of interest is experiencing the pain condition or the no-pain condition, wherein applying the trained N-CNN to the image data captured by the video image capture device comprises preprocessing the image data of the face of the neonate of interest to generate a plurality of preprocessed frames focused on the face of the neonate of interest, performing a combination of a convolution layer and a max pooling operation on each of the plurality of preprocessed frames at a right branch of the N-CNN to extract prominent features from the plurality of preprocessed frames, at a left branch of the N-CNN to extract generic features from the plurality of preprocessed frames and at a central branch of the N-CNN to extract deep features from the plurality of preprocessed frames, merging the prominent features from the plurality of preprocessed frames extracted at the right branch, the generic features extracted at the left branch and the deep features extracted at the central branch to generate merged results and performing a combination of convolution and max pooling of the merged results to determine if the neonate of interest is experiencing the pain condition or the no-pain condition, and providing an output from the N-CNN indicating whether the neonate of interest is experiencing the pain condition or the no-pain condition.

\* \* \* \* \*